United States Patent
Schaefer et al.

(10) Patent No.: US 10,578,528 B2
(45) Date of Patent: Mar. 3, 2020

(54) COMPRESSION TEST FIXTURE AND METHOD THEREFOR

(71) Applicant: THE BOEING COMPANY, Chicago, IL (US)

(72) Inventors: Joseph D. Schaefer, St. Louis, MO (US); Brian P. Justusson, St. Peters, MO (US); Brian Kasperson, Seattle, WA (US); David R. Barbee, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 304 days.

(21) Appl. No.: 15/447,245

(22) Filed: Mar. 2, 2017

(65) Prior Publication Data

US 2018/0252625 A1   Sep. 6, 2018

(51) Int. Cl.
*G01N 3/08* (2006.01)
*G01N 3/02* (2006.01)
*G01N 33/00* (2006.01)

(52) U.S. Cl.
CPC .............. *G01N 3/08* (2013.01); *G01N 3/02* (2013.01); *G01N 33/00* (2013.01); *G01N 2033/0003* (2013.01)

(58) Field of Classification Search
CPC ............. G01N 2/08; G01N 2/02; G01N 33/00
USPC .......................................................... 73/818
See application file for complete search history.

(56) References Cited

U.S. PATENT DOCUMENTS

| 3,916,681 | A | * | 11/1975 | Ryckman | G01N 3/04 73/800 |
| 4,662,229 | A | * | 5/1987 | Curtis | G01N 3/04 73/859 |
| 4,840,070 | A | * | 6/1989 | Ralfs | G01N 3/02 73/818 |
| RE33,409 | E | * | 10/1990 | Curtis | G01N 3/04 73/859 |
| 5,176,028 | A | * | 1/1993 | Humphrey | B29C 65/18 374/45 |
| 5,297,441 | A | * | 3/1994 | Smith | G01N 3/04 73/818 |
| 5,355,683 | A | * | 10/1994 | Taylor | G01N 3/04 250/443.1 |

(Continued)

OTHER PUBLICATIONS

TestResources, Inc. "ASTM D695 Compression Testing for Rigid Plastics" 2017. www.testresources.net/applications/standards/astm/astm-d695-compression-testing-for-rigid-plastics/.

(Continued)

*Primary Examiner* — Nathaniel T Woodward
(74) *Attorney, Agent, or Firm* — Perman & Green, LLP

(57) ABSTRACT

A compression test fixture including a first specimen engagement member having a first channel, the first channel having a first depth; a second specimen engagement member having a second channel having a second depth that is different than the first depth; and at least one coupling member engaged to both the first specimen engagement member and the second specimen engagement member such that a gap is defined between the first specimen engagement member and the second specimen engagement member, where the first channel and the second channel support the test specimen within the gap such that at least one opposing major surface of the test specimen is visible within the gap.

20 Claims, 12 Drawing Sheets

(56) References Cited

U.S. PATENT DOCUMENTS

| | | | | |
|---|---|---|---|---|
| 5,361,640 A * | 11/1994 | Carroll | G01N 3/04 33/790 |
| 5,459,767 A * | 10/1995 | Lessing | G01N 3/565 100/99 |
| 5,581,040 A * | 12/1996 | Lin | G01N 3/04 73/833 |
| 5,811,686 A * | 9/1998 | Lavoie | G01N 3/08 73/821 |
| 5,945,607 A * | 8/1999 | Peppel | G01N 3/04 73/831 |
| 6,332,364 B1 * | 12/2001 | Buschmann | G01N 3/08 73/788 |
| 6,422,090 B1 * | 7/2002 | Ferguson | B21J 9/20 73/795 |
| 6,526,837 B1 * | 3/2003 | Grote | G01N 3/04 73/856 |
| 2005/0011275 A1 * | 1/2005 | Ferguson | G01N 3/04 73/818 |
| 2011/0314926 A1 * | 12/2011 | Hanabusa | G01N 3/04 73/826 |
| 2013/0042696 A1 * | 2/2013 | Fukuda | G01N 3/04 73/800 |
| 2014/0150564 A1 * | 6/2014 | Brandt | G01N 3/08 73/818 |

OTHER PUBLICATIONS

Wyoming Test Fixtures, Inc. "Compression Subpress (ASTM D 695) Model No. WTF-SP (17-4PH stainless steel)" 2017. www.wyomingtestfixtures.com/Products/b11.html.

Institute of Applied Mechanics, RWTH AACHEN University. "Laboratory Equipment" Updated: Jun. 13, 2016. http://www.ifam.rwth-aachen.de/aw/cms/IFAM/Themen/~vzb/experimentelle-ausstattung2/?lang=en.

Intertek Plastics Technology Laboratories "Compressive Properties of Polymet Matrix Composite Laminates Using a Combined Loading Compression (CLC) Test Fixture ASTM D6641" 2017. http://www.ptli.com/testlopedia/tests/Compression-ASTM-D6641.asp.

Koerber, et al. "High strain rate characterisation of unidirectional carbon-epoxy IM7-8552 in transverse compression and in-plane shear using digital image correlation" Elsevier, Mechanics of Materials, vol. 42, Issue 11, pp. 1004-1019, 2010. http://dx.doi.org/10.1016/j.mechmat.2010.09.003.

* cited by examiner

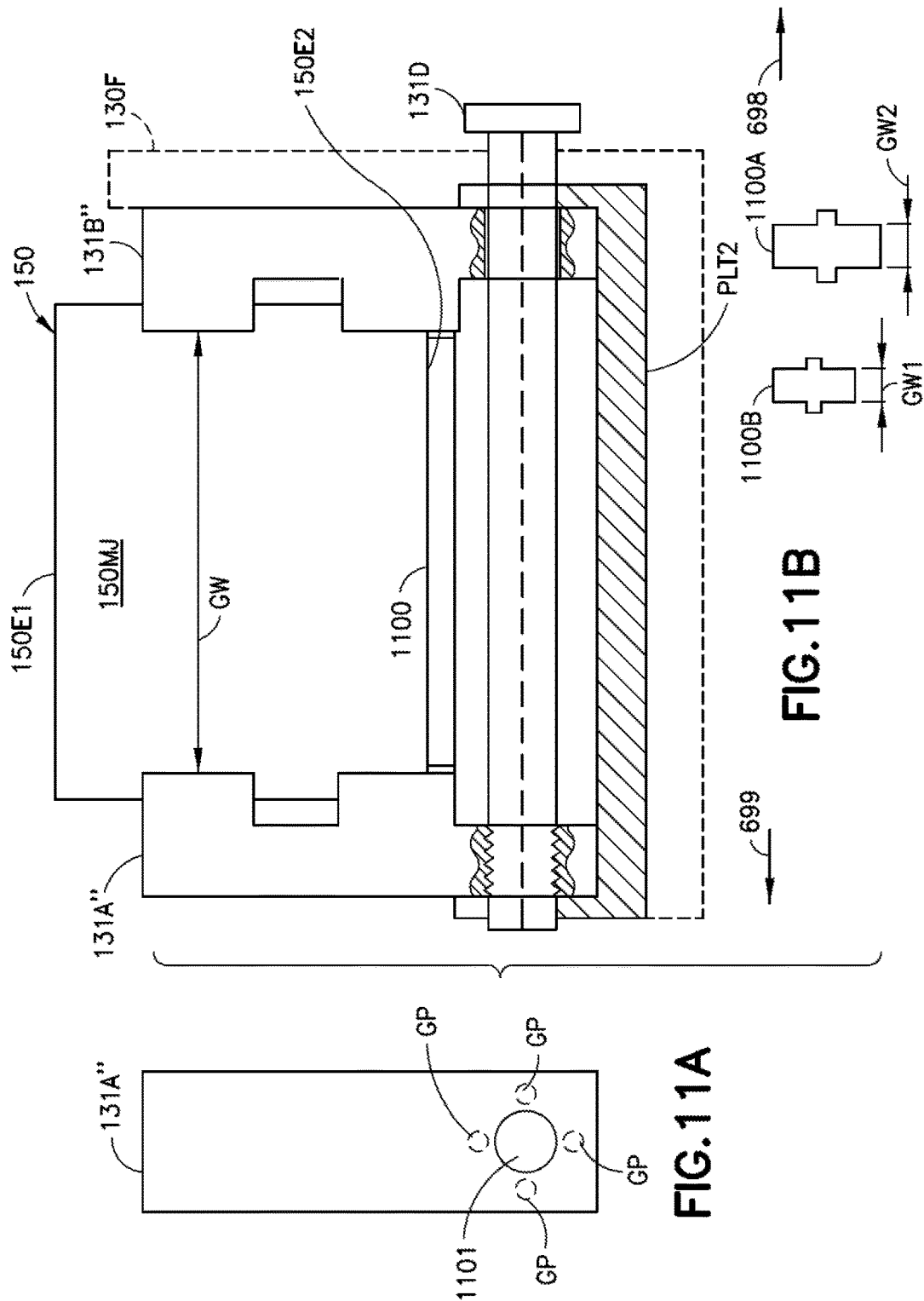

COMPRESSION TEST FIXTURE AND METHOD THEREFOR

The disclosure described herein was made in the performance of work under National Aeronautics and Space Administration (NASA) Contract No, ACC C15-2A38, subcontract number ACC 2C06-1.2.1 and is subject to the provisions of Section 305 of the National Aeronautics and Space Act of 1958 (72 Stat. 435: 42 U.S.C. 2457). NASA has certain rights in this application.

BACKGROUND

1. Field

The exemplary embodiments generally relate to compression testing and in particular to compression testing of composites.

2. Brief Description of Related Developments

Compression testing of, for example, test specimens including a series of lamina containing fibers oriented at an angle to the loading axis, or multiply laminates comprised of multiple ply orientations relative to the loading axis is desired. These test specimens including the series of unidirectional lamina containing fibers at an angle to the loading axis may be referred to as "off-axis" test specimens. The off-axis test specimens are tested in compression to induce states of coupled transverse normal compression and in-plane shear (e.g. in a 1-2 plane where direction 1 is a direction of the fibers in the composite material being tested and direction 2 is a direction transverse to plane 1 along a major surface of the test specimen). Generally, the off-axis test specimens are tested in a conventional compression test fixture, such as the ASTM D695 compression test fixture. The conventional compression test fixtures were initially used to and hold the test specimen during testing; however, the conventional compression test fixtures are inadequate for testing the off-axis test specimens due to the visual obstruction of the specimen surface by the conventional compression test fixtures. For example, the conventional compression test fixtures generally use a pair of I-shaped fixture members that are bolted together with the test specimen sandwiched between the pair of I-shaped fixture members. The major surfaces of the test specimen are positioned against surfaces of the I-shaped fixture members to prevent buckling of the test specimen while under compression during testing of the test specimen; however, placement of the major surfaces against the I-shaped fixture members occludes the major surfaces from view such that conventional compression test fixtures generally do not allow for width-wise viewing of the test specimen, such as in the 1-2 plane. The minor surfaces of the test specimen are exposed to allow expansion of the test specimen while under a compression load. While the conventional compression test fixtures provide for obtaining basic compression strain and failure data (using measurement techniques such as axial edge-mounted extensometers), due to the visual obstruction of the specimen surface in the 1-2 plane, advanced inspection techniques cannot be used with the conventional compression test fixtures. Further, conventional compression test fixtures do not provide enough spacing for axial load application to the off-axis test specimens in the testing machine.

In addition, due to the I-shaped attire members, the aspect ratio of the test specimen is required to be a prescribed size such that the test specimen has a predetermined height and width, thus preventing testing of test specimens having varying widths or lengths.

If one departs from the use of the conventional test fixtures, so as to hold the test specimen only at the ends of the test fixture, rather than sandwich the test specimen between two fixture members, the test specimen may fail at one of the ends and/or buckle such that the test may not provide the desired compression data.

SUMMARY

The following is a non-exhaustive list of examples, which may or may not be claimed, of the subject matter according to the present disclosure.

One example of the subject matter according to the present disclosure relates to a compression test fixture comprising a first specimen engagement member having a first channel, the first channel having a first depth; a second specimen engagement member having a second channel having a second depth that is different than the first depth; and at least one coupling member engaged to both the first specimen engagement member and the second specimen engagement member such that a gap is defined between the first specimen engagement member and the second specimen engagement member, where the first channel and the second channel support the test specimen within the gap such that at least one opposing major surface of the test specimen is visible within the gap.

Another example of the subject matter according to the present disclosure relates to a compression test system comprising a frame; and a test fixture coupled to the frame, the test fixture includes a first specimen engagement member having a first channel, the first channel having a first depth: a second specimen engagement member having a second channel having a second depth that is different than the first depth; and at least one coupling member engaged to both the first specimen engagement member and the second specimen engagement member such that a gap is defined between the first specimen engagement member and the second specimen engagement member, where the first channel and the second channel support the test specimen within the gap such that opposing major surfaces of the test specimen are visible within the gap.

Still another example of the subject matter according to the present disclosure relates to a method for performing a compression test on a test specimen, the method comprising defining a gap between a first specimen engagement member and a second specimen engagement member of a compression test fixture with at least one coupling member engaged to both the first specimen engagement member and the second specimen engagement member, where the first specimen engagement member has a first channel having a first depth, and the second specimen engagement member has a second channel having a second depth that is different than the first depth; inserting a test specimen into the first channel and the second channel such that the first channel and the second channel support the test specimen within the gap such that opposing major surfaces of the test specimen are visible within the gap; and applying a compression load to the test specimen.

BRIEF DESCRIPTION OF THE DRAWINGS

Figure 1A:
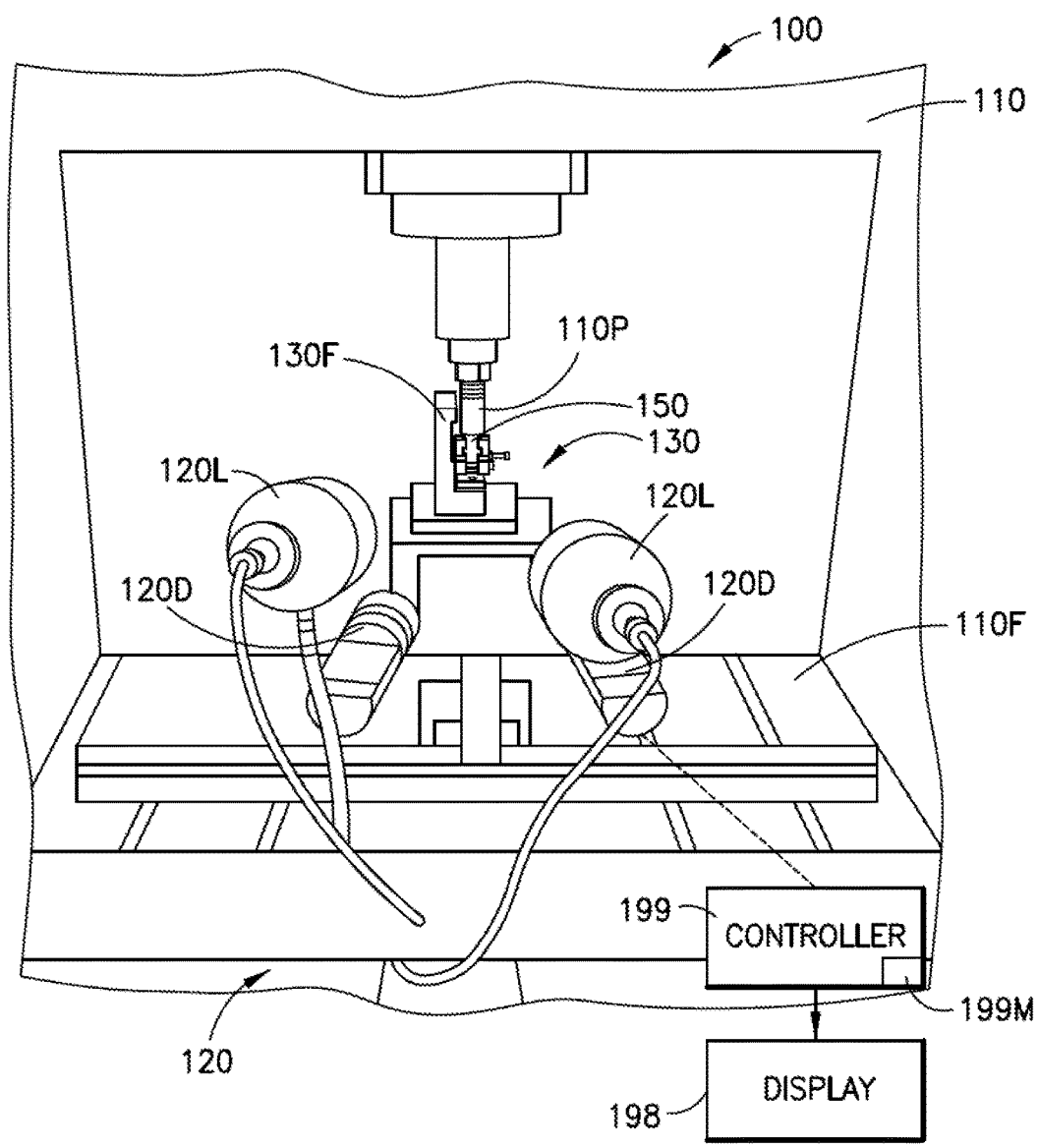
Figure 1B:
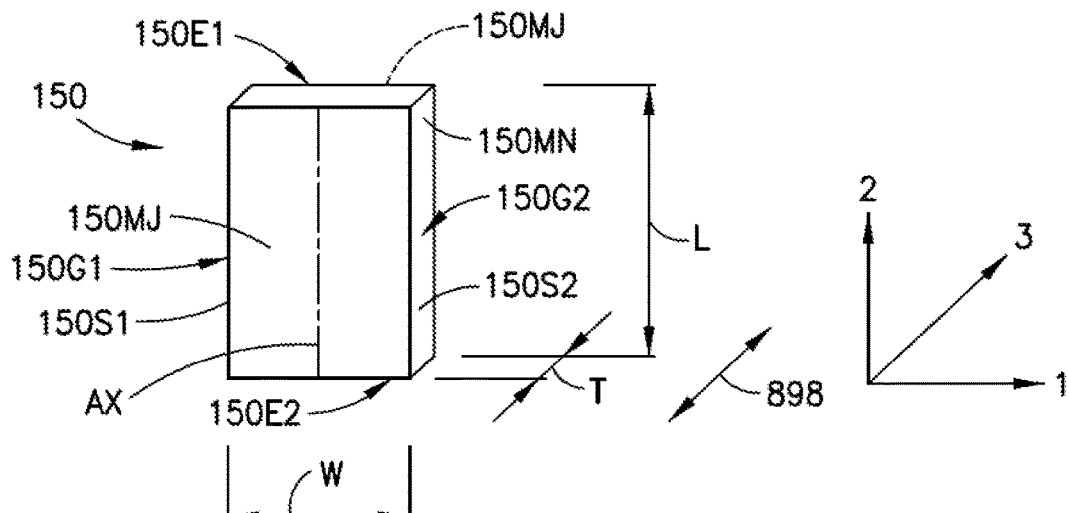
Figure 1C:
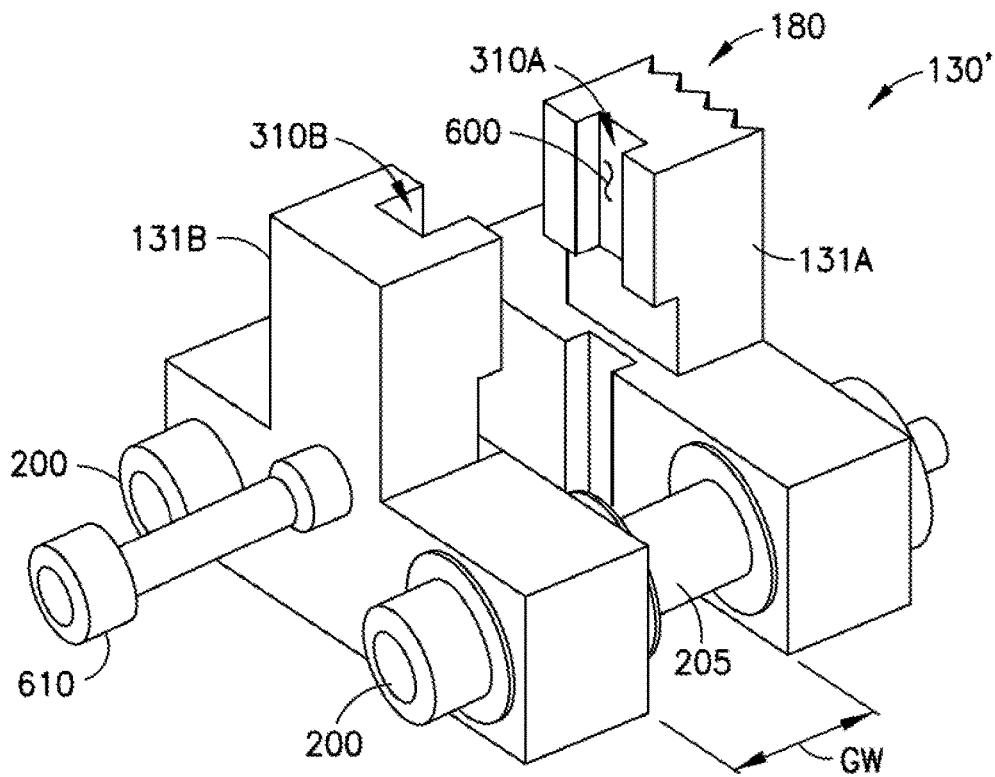
Figure 1D:
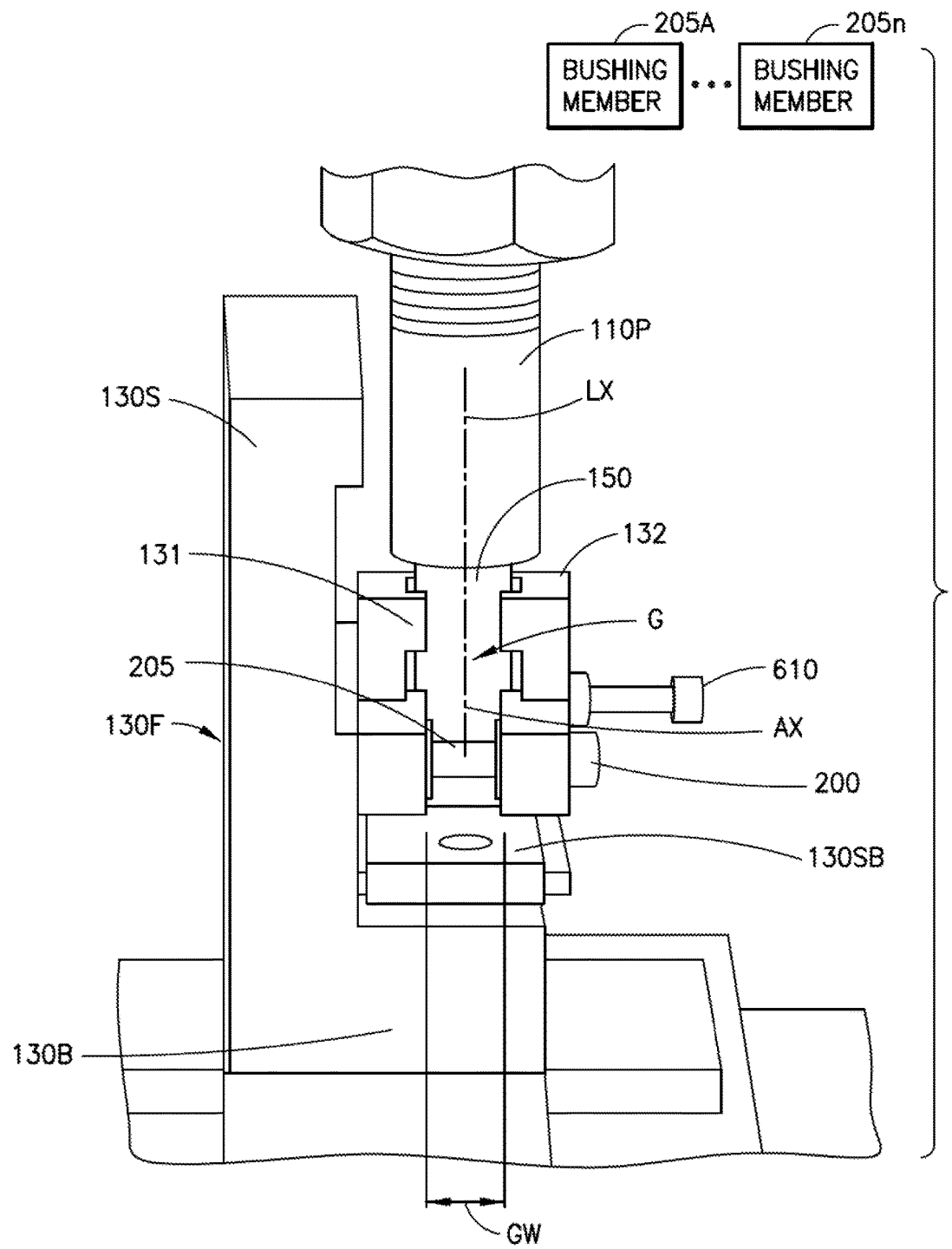
Figure 2A:
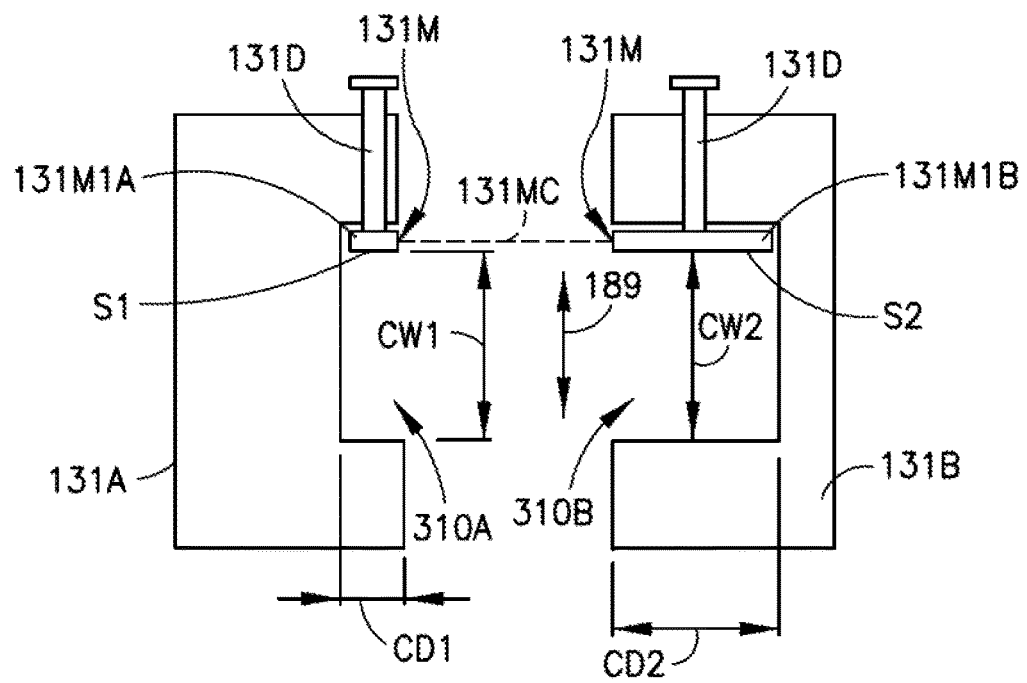
Figure 2B:
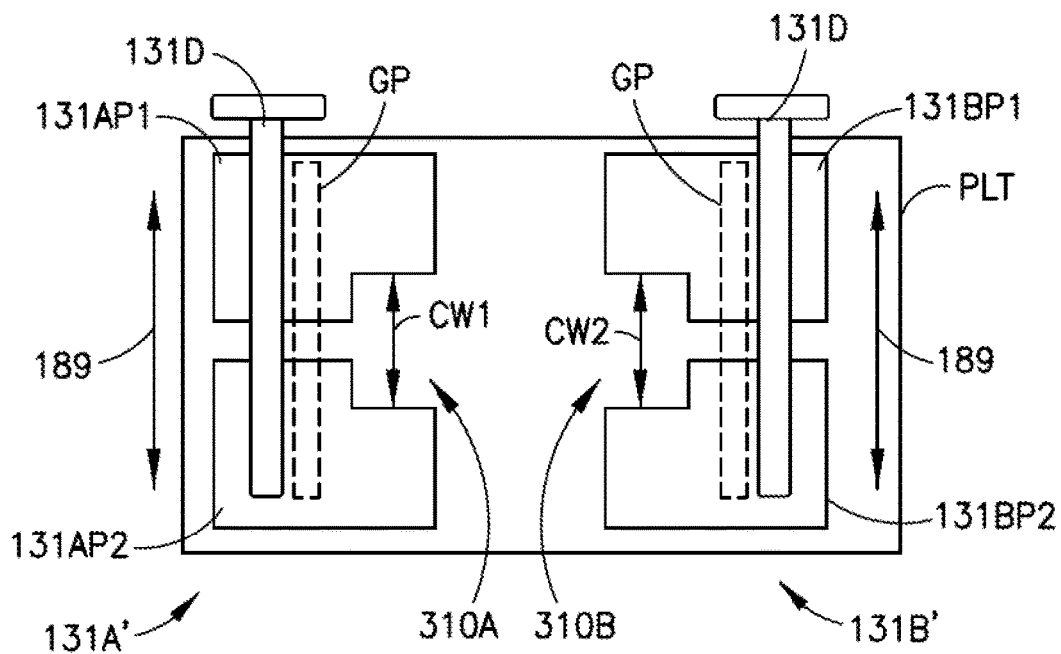
Figure 2C:
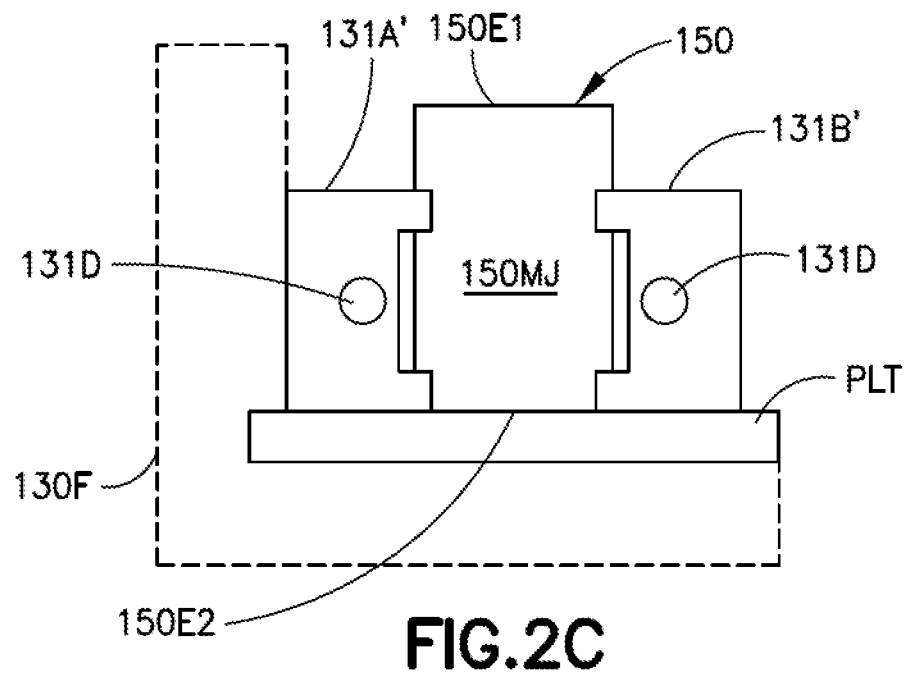
Figure 3:
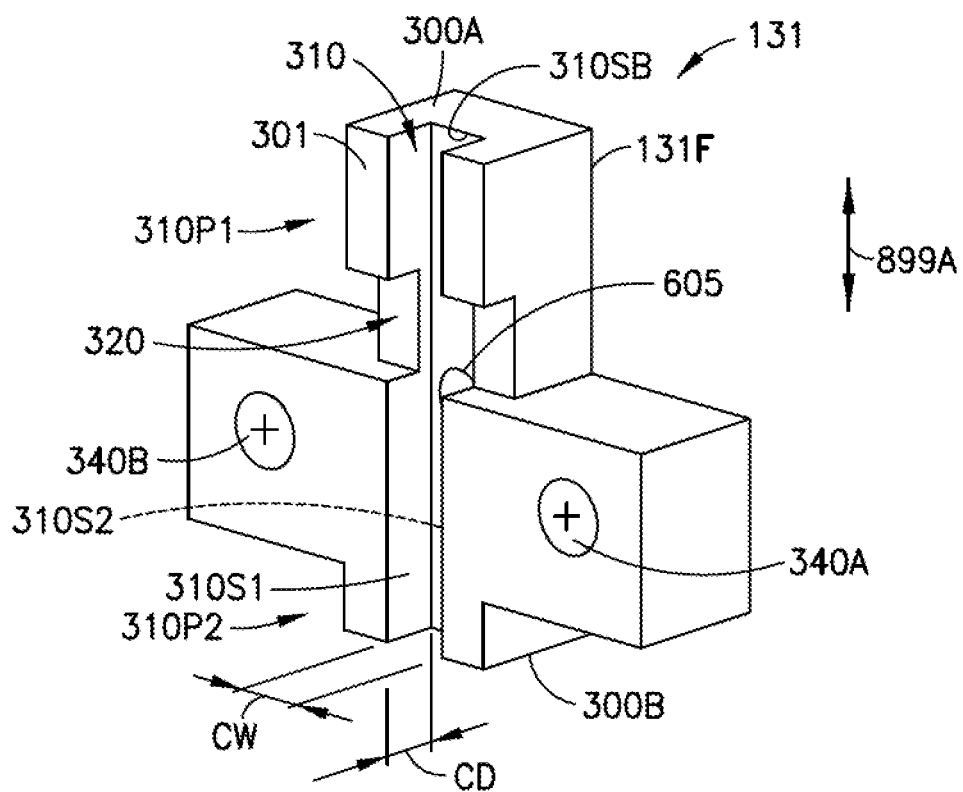
Figure 4:
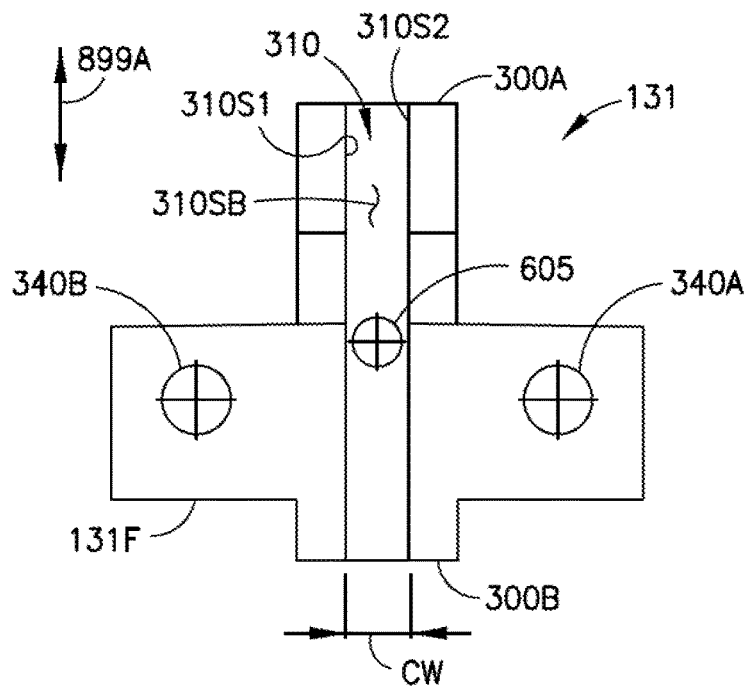
Figure 5:
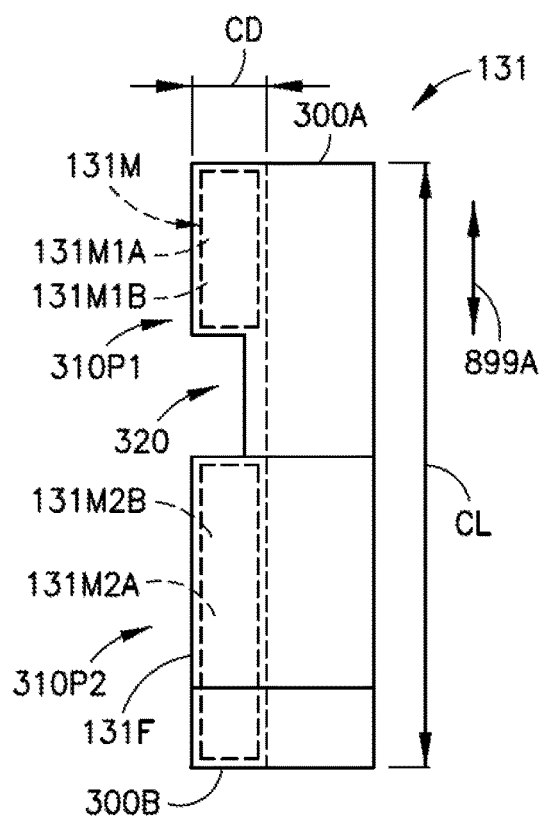
Figure 6:
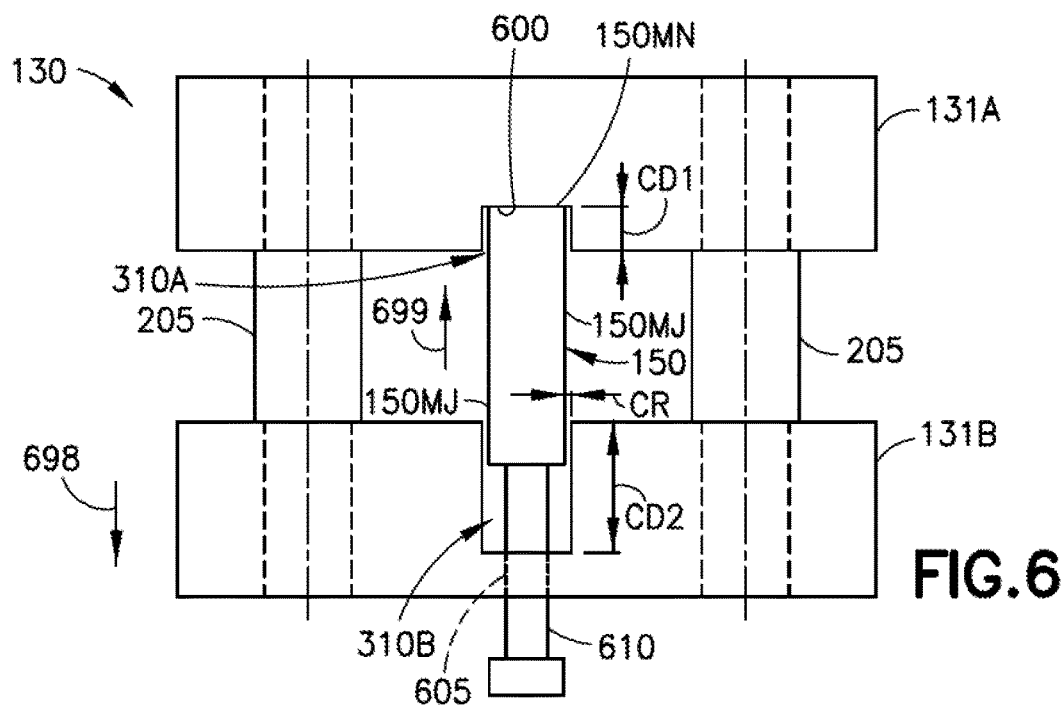
Figure 7:
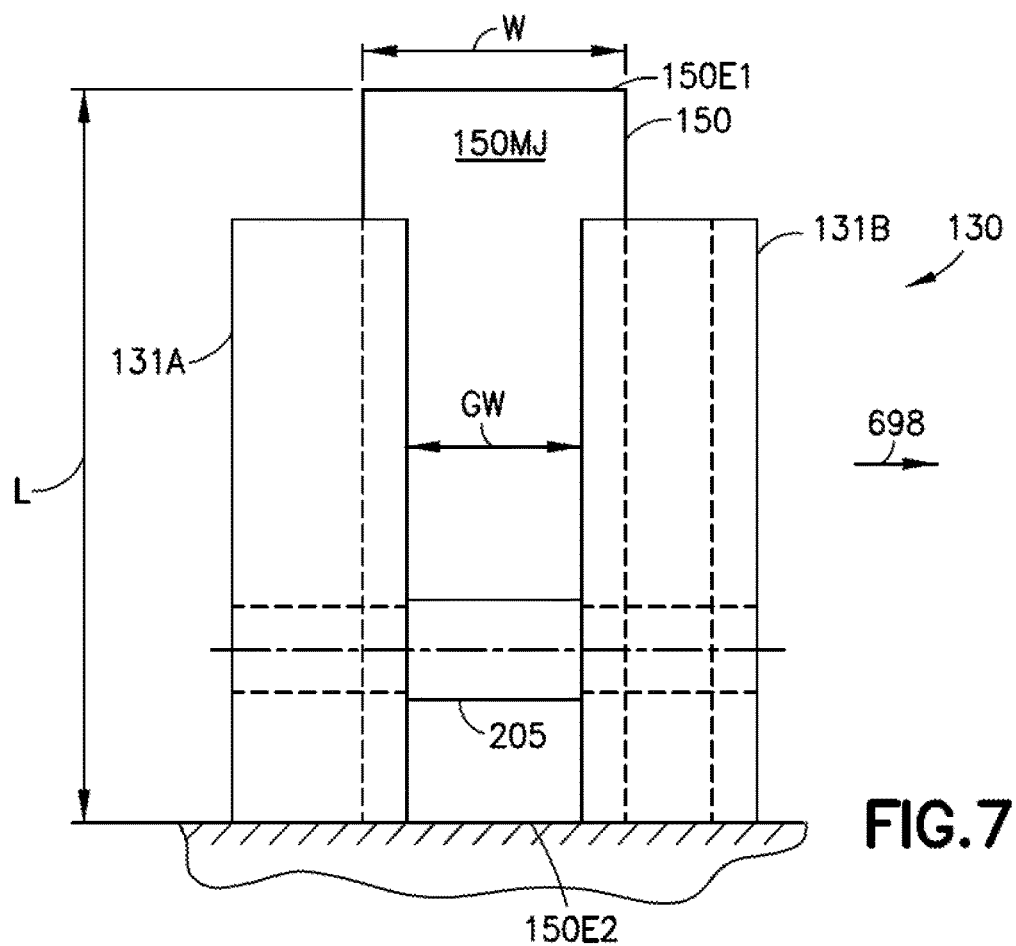
Figure 8C:
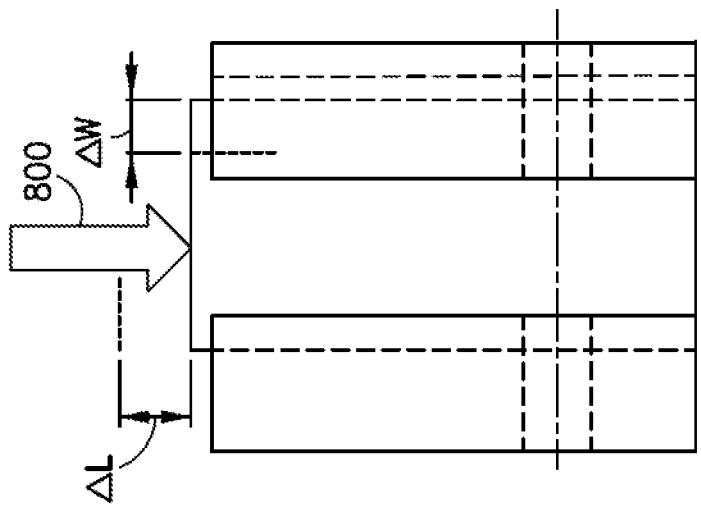
Figure 8B:
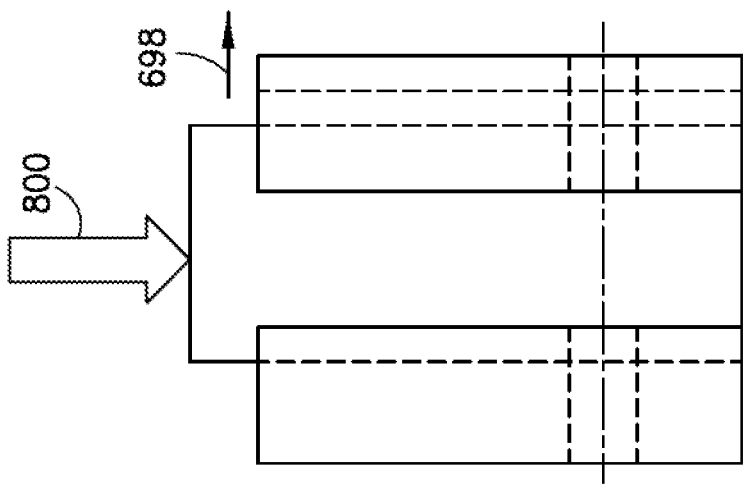
Figure 8A:
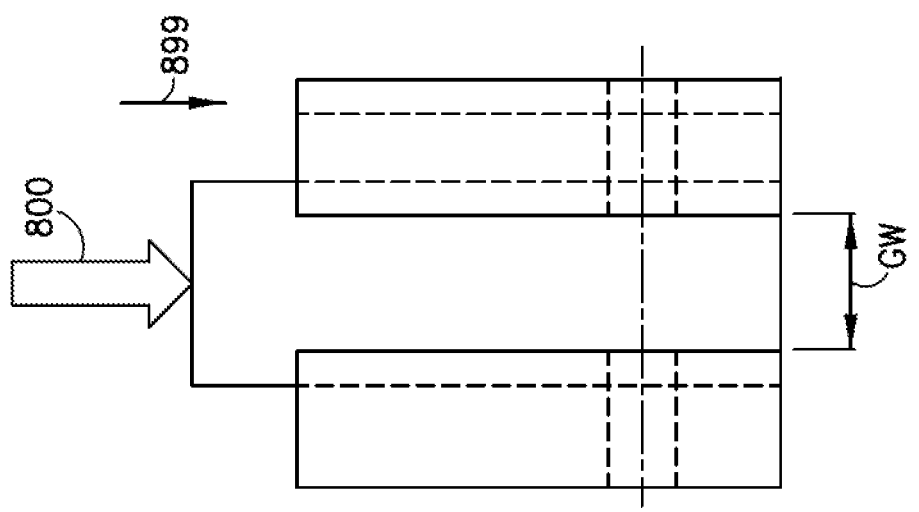
Figure 9:
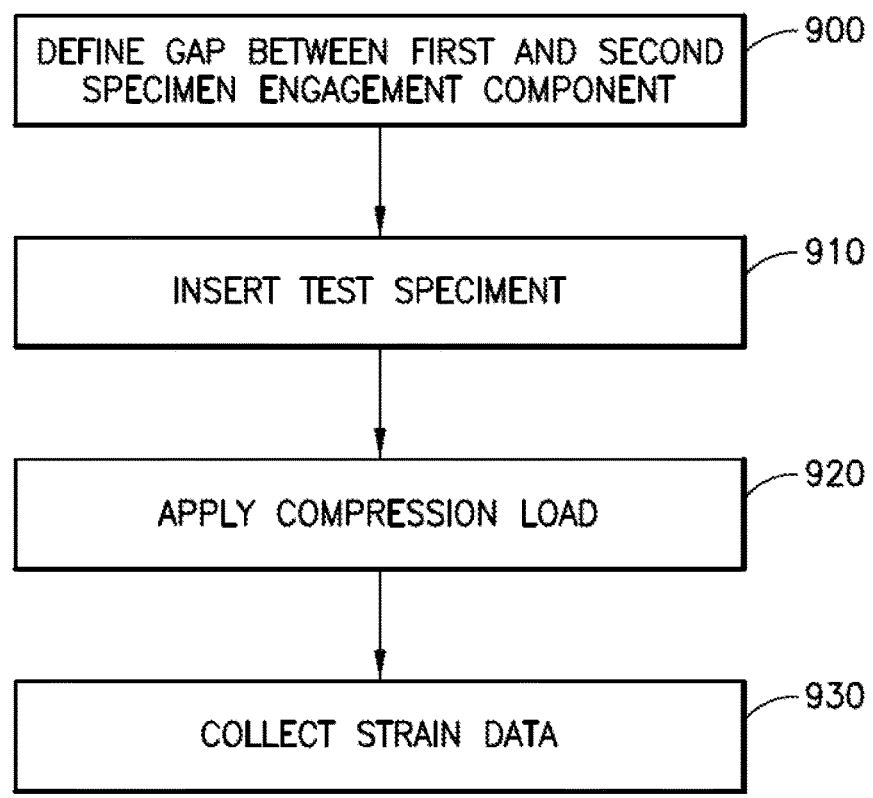
Figures 10A, 10B:
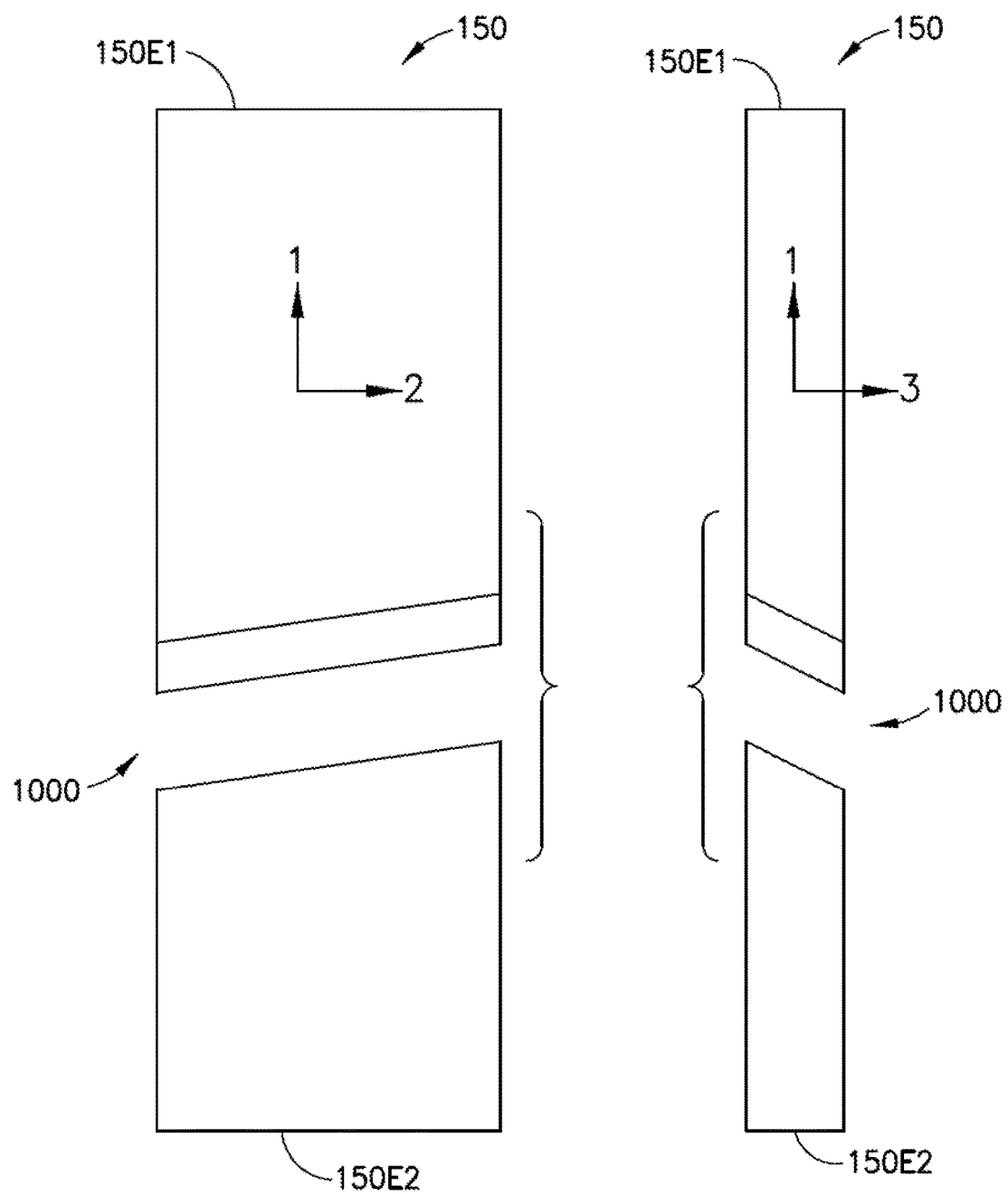
Figure 11C:
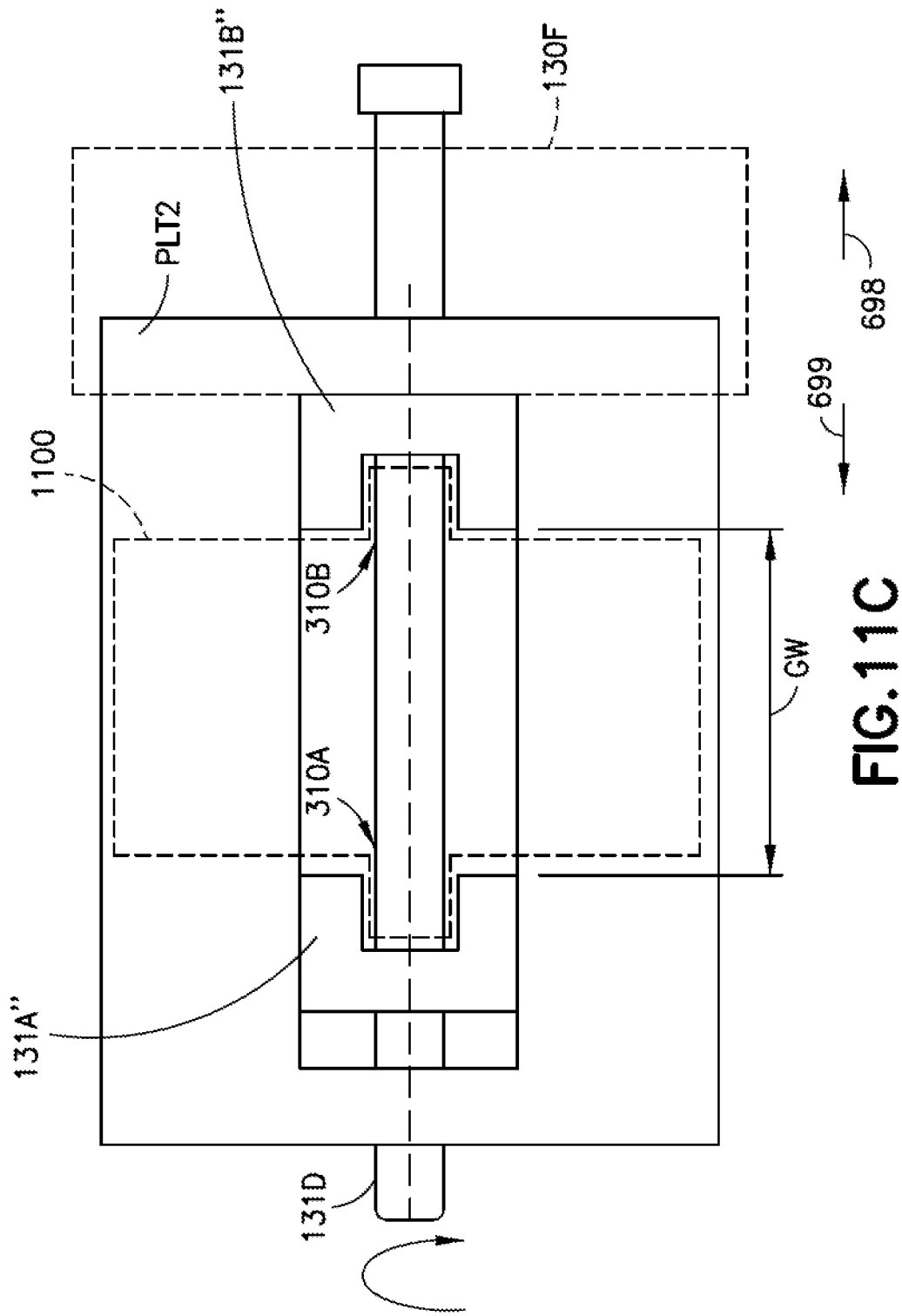

Having thus described examples of the present disclosure in general terms, reference will now be made to the accompanying drawings, which are not necessarily drawn to scale, and wherein like references characters designate the same or similar parts throughout the several views, and wherein:

FIG. 1A is a schematic illustration of a compression test system including a compression test fixture in accordance with aspects of the present disclosure;

FIG. 1B is a schematic illustration of a test specimen in accordance with aspects of the present disclosure;

FIG. 1C is a schematic illustration of a compression test fixture in accordance with aspects of the present disclosure;

FIG. 1D is a schematic illustration of a portion of the compression test system in accordance with aspects of the present disclosure;

FIG. 2A is a schematic illustration of a portion of the compression test fixture of FIGS. 1C and 1D in accordance with aspects of the present disclosure;

FIGS. 2B and 2C are schematic illustrations of a portion of the compression test fixture of FIGS. 1A, 1C and 1D in accordance with aspects of the present disclosure;

FIG. 3 is a schematic isometric view illustration of a portion of the compression test fixture illustrated in FIGS. 1A, 1C and 1D in accordance with aspects of the present disclosure;

FIG. 4 is a schematic front view illustration of the portion of the compression test fixture of FIG. 3 in accordance with aspects of the present disclosure;

FIG. 5 is a schematic side view illustration of the portion of the compression test fixture of FIG. 3 in accordance with aspects of the present disclosure;

FIG. 6 is a schematic top view illustration of the compression test fixture illustrated in FIGS. 1A, 1C and 1D in accordance with aspects of the present disclosure;

FIG. 7 is a schematic front view illustration of the compression text fixture illustrated in FIGS. 1A, 1C and 1D in accordance with aspects of the present disclosure;

FIGS. 8A, 8B and 8C are schematic front view illustrations of the compression text fixture illustrated in FIGS. 1A, 1C and 1D showing different stages of test specimen compression in accordance with aspects of the present disclosure;

FIG. 9 is an exemplary flow diagram in accordance with aspects of the present disclosure;

FIG. 10A is a schematic front view illustration of a test specimen after compression testing in accordance with aspects of the present disclosure;

FIG. 10B is a schematic side view illustration of a test specimen after compression testing in accordance with aspects of the present disclosure; and FIGS. 11A-11C are schematic illustrations of a portion of the compression test fixture of FIGS. 1A, 1C and 1D in accordance with aspects of the present disclosure.

DETAILED DESCRIPTION

Referring to FIGS. 1A, 1B and 1D, the aspects of the present disclosure described herein may allow a test specimen (also known as a test coupon) 150 to be compression tested using any suitable data collection system 120 (including at least one sensing device 120D such as, cameras, strain gages, extensometers, etc.) such as a standard data collection system and/or any suitable advanced data collection systems, such as digital image correlation (DIC) system where data is collected, the test specimen 150 is viewed and the data is analyzed in-situ (i.e. during testing). The aspects of the present disclosure provide a compression test system 100 and a compression test fixture 130 with a pair of specimen engagement members (a first specimen engagement member 131A and a second specimen engagement member 131B) that support the test specimen 150 such that both major surfaces 150MJ of the test specimen are visible through a gap G in the compression test fixture 130 so that data of, for example, strain in at least one of the major surfaces 150MJ can be gathered using the data collection system 120. In one aspect, the compression test fixture 130 described herein, in accordance with the aspects of the present disclosure, may not cause failure of the test specimen 150 at the ends 150E1, 150E2 of the test specimen 150, where the test specimen 150 may not be visible. In accordance with the aspects of the present disclosure, each of the first and second specimen engagement members 131A, 131B includes a channel (see the first channel 310A and the second channel 310B) into which a respective side (first side 150S1 and second side 150S2) of the test specimen 150, each defining a minor surface 150MN of the test specimen 150, is inserted. The channel in one of the first specimen engagement member 131A and the second specimen engagement member 131B is deeper than the channel 310A, 310B in the other one of the first specimen engagement member 131A and the second specimen engagement member 131B to provide for sideways movement or width-wise expansion of the test specimen 150 within the deeper channel when a compression load is applied to the test specimen 150. One of the first channel 310A and the second channel 310B being deeper than the other also provides for testing test specimens 150 having varying widths W and may provide anti-buckling support of the test specimens 150. A width of the channel may also be adjustable to provide for testing test specimens 150 having varying thicknesses T. The first and second channels 310A, 310B in the first and second specimen engagement members 131A, 131B also provide for simple and repeatable alignment of the test specimens 150 to enhance data collection accuracy. The aspects of the present disclosure also provide for a modular compression test fixture 130 that may be retrofit to conventional fixturing systems such as the D695 compression fixture, a separate stabilizing fixture, or as a standalone system.

Illustrative, non-exhaustive examples, which may or may not be claimed, of the subject matter according to the present disclosure are provided below.

Referring to FIGS. 1A and 1B an exemplary compression test system 100 is illustrated incorporating aspects of the present disclosure. In one aspect, the compression test system 100 includes a press 110, a data collection system 120 and a compression test fixture 130. In one aspect, the press 110 is a hydraulic press but in other aspects any suitable press may be used to apply a compression load to a test specimen 150 held by the compression test fixture 130. In one aspect, the press 110 includes a frame 110F to which the compression test fixture 130 is coupled. The press 110 includes a platen 110P, constructed of any suitable material such as hardened steel, that engages the test specimen 150 held by the compression test fixture 130.

In one aspect, the data collection system 120 is disposed adjacent to the compression test fixture 130 such that at least one of the opposing major surfaces 150MJ of the test specimen 150 are viewed by the data collection system 120. In one aspect, the data collection system 120 includes any suitable number of light sources 120L and at least one sensing device 120D, which in one aspect is any suitable number of digital imaging devices that provide signals that embody compression data, such as strain data, to any suitable controller 199. The controller 199 is configured to determine strain measurement on the test specimen 150 from the compression load applied to the test specimen 150 by the press 110 and output the strain measurement to any suitable display 198 for viewing and/or analysis during the compression testing of the test specimen 150. The controller 199 may also include any suitable memory 199M configured to record the compression data and strain measurements determined therefrom for viewing/reviewing after compression testing of the test specimen 150 is completed.

The compression test fixture 130 is configured to hold a test specimen 150 that has a general hexahedron shape but in other aspects, the test specimen may have any suitable shape. For example, the test specimen 150 includes two major surfaces 150MJ with four minor surfaces 150MN disposed therebetween. The Each of the major surfaces 150MJ has a width W and a length L in which the 1-2 plane of the test specimen exists (again noting that direction 1 is the direction of the fibers in the composite material being tested and direction 2 is a direction transverse to plane 1 along a major surface of the test specimen, while direction 3 is in the direction of the thickness T of the test specimen 150). Two of the minor surfaces 150MN form the ends 150E1, 150E2 of the test specimen and have a thickness T and the width W. The other two minor surfaces 150MN form the first side 150S1 and the second side 150S2, each having the length L and the thickness T. In one aspect, the test specimen 150 is an off-axis specimen of composite laminate where the major symmetry axes, such as major symmetry axis AX, of the laminate are aligned with the loading axis LX. In other aspects, the test specimen may be any suitable test specimen constructed of any suitable test material (e.g. composites, metals, plastics, ceramics, glass, etc.).

In one aspect, the compression text fixture 130 includes any suitable fixture frame 130F that is configured to couple with the frame 110F of the press 110 in any suitable manner. For example, the fixture frame 130F may be clamped or bolted to the frame 110F. In one aspect, the fixture frame 130F includes a base 130B and a stanchion 130S extending from the base 130B. In one aspect, the base 130B includes a removable and replaceable specimen support 130SB coupled to the base 130B in any suitable manner and being configured to locate and engage one end 150E1, 150E2 of the test specimen 150.

Referring to FIGS. 1C, 1D and 3-5, the compression test fixture also includes the first specimen engagement member 131A and the second specimen engagement member 131B. In one aspect, the first specimen engagement member 131A and the second specimen engagement member 131E are substantially mirror images of each other and will be described with respect to specimen engagement member 131 illustrated in FIGS. 3-5; however in other aspects the first specimen engagement member 131A and the second specimen engagement member 131E may not be mirror images of each other and may each have any suitable shape and size. It should also be understood that the shape of the specimen engagement member 131 is exemplary in nature and in other aspects, the specimen engagement member 131 may have any suitable shape that provides anti-buckling support for and viewing of the major surfaces of the test specimen 150. In one aspect, the specimen engagement member 131 includes a specimen engagement member frame 131F having a first end surface 300A and a second end surface 300B separated from each other by a length CL of the specimen engagement member frame 131F. In one aspect, the length CL is less than the length L of the test specimen 150 by any suitable amount so that the test specimen 150 can be compressed for testing. In one aspect, the length CL depends on an amount of expansion expected as the test specimen 150 is compressed and/or the stiffness of the test specimen 150. In one aspect, the length CL is about 10% to about 20% smaller than the length L of the test specimen before compression of the test specimen 150; however, in other aspects, the length CL may be less than about 10% smaller than the length L of the test specimen 150 before compression or greater than about 20% smaller than the length L of the test specimen 150 before compression. A side surface 301 of the specimen engagement member frame 131F extends between the first end surface 300A and the second end surface 300B. The specimen engagement member frame 131F is shaped so as to form a channel 310 that extends between the first end surface 300A and the second end surface 300B such that the channel 310 is defined in each of the first end surface 300A, the second end surface 300B and the side surface 301 such that the test specimen can extend from the first end surface 300A and be supported by the specimen support 130SB of the fixture frame 130F or a support surface of the press 110 such as when the compression test fixture 130 is used as a stand-alone compression test fixture 130' as described herein. The channel 310 is defined such that sides 310S1, 310S2 define a width CW of the channel 310 and side 310SB defines, with the side surface 301, a depth CD of the channel 310. In one aspect, the width CW corresponds to the width W of the test specimen 150 such that minimal clearance CR (see FIG. 6) exists between the test specimen 150 and the sides 310S1, 310S2 to allow movement of the test specimen 150 in direction 899A and to prevent buckling of the test specimen 150 when a compression load is applied to the test specimen 150. In one aspect, the specimen engagement member frame 131F includes one or more recess 320 that intersects the channel 310 and separates a first portion 310P1 of the channel 310 adjacent the first end surface 300A from a second portion 310P2 of the channel 310 adjacent the second end surface 300B such that an edge 150G1, 150G2 (defined by the intersections between the major surfaces 150MJ and the minor surfaces 150MN of the test specimen 150 along the length L) is visible within the recess 320.

In one aspect, with reference to FIGS. 2A and 5 one or more of the first specimen engagement member 131A and the second specimen engagement member 131B includes at least one support member 131M movably disposed within the channel 310, For example, in one aspect, a position of the at least one support member 131M within the first channel 130A of the first specimen engagement member 131A defines width CW1 of the first channel 130A. In one aspect, the at least one first support member 131M includes an alignment surface S1 that engages with and locates a major surface 150MJ of the test specimen 150 in the compression test fixture such that the test specimen 150 is supported from buckling during compression testing of the test specimen 150. In one aspect, the at least one support member 131M of the second specimen engagement member 131E is movably disposed within the second channel 310B, where a position of the at least one support member 131M within the second channel defines a width CW2 of the second channel 310B. In one aspect, the at least one support member of each of the first the specimen engagement members 131A and the second the specimen engagement members 131B includes a support member 131M1A, 131M1B disposed at a first end of the channel 310 adjacent the first end surface and another support member 131M2A, 131M2B disposed at a second end of the channel 310 adjacent the second end surface 300B. In one aspect, the at least one support member 131M of the first specimen engagement member 131A is coupled to the at least one support member 131M of the second specimen engagement member 131B by any suitable coupling 131MC (e.g. such as a bar, rods, etc.) so as to be movable as a one piece member. In one aspect, the support member 131M1A disposed at the first end of the first channel 310A of the first specimen engagement member 131A is coupled to the support member 131M1B disposed at the first end of the second channel 310B of the second specimen engagement member 131B by any suitable coupling 131MC so as to be movable as a one piece member. In one aspect, the other support member 131M2A disposed at the second end of the first channel 310A is coupled to the other support member 131M2B disposed at the second end of the second channel 310B by any suitable coupling 131MC so as to be movable as a one piece member. In one aspect, any suitable screw drive 131D, such as a jack screw, may be used to move the at least one support member 131M of the first specimen engagement member 131A and the second specimen engagement member 131B within the respective channel 310A, 310B in direction 189 to adjust a the width CW1, CW2 of the respective channel 310A, 310B.

In one aspect the specimen engagement member frame 131F includes coupling features such as one or more apertures 340A, 340B through which at least one coupling member 200 passes for coupling each of the first specimen engagement member 131A and the second specimen engagement member 131B together and/or to the fixture frame 130F. In one aspect, the at least one coupling member 200 includes a fastener, such as a threaded bolt or socket head cap screw, extending through one of the first specimen engagement member 131A and the second specimen engagement member 131B and into the other one of the first specimen engagement member 131A and the second specimen engagement member 131B. In one aspect, the at least one coupling member 200 couples the first specimen engagement member 131A and the second specimen engagement member 131B to the fixture frame 130F such that a first channel 310A of the first specimen engagement member 131A and a second channel 310B of the second specimen engagement member 131B face each other in an opposing relationship. As can be seen in FIG. 1D a coupling member 200 may pass through a respective aperture 340A, 340B in the second specimen engagement member 131B and through a corresponding aperture 340A, 340B in the first specimen engagement member 131A where the fastener engages the fixture frame 130F in any suitable manner, such as a threaded engagement, for coupling both the first specimen engagement member 131A and the second specimen engagement member 131B to the fixture frame 130F. In other aspects, the first specimen engagement member 131A may be coupled to the fixture frame 130F and the second specimen engagement member 131B may be coupled to the first specimen engagement member 131A in any suitable manner. In one aspect, as illustrated in FIG. 1C, where the first specimen engagement member 131A and the second specimen engagement member 131B form a stand-alone compression test fixture 130', that is substantially similar to compression test fixture 130 but coupled substantially directly to the frame 110F of the press 110 in any suitable manner without for example, a fixture frame 130F, the at least one coupling member 200 couples the first specimen engagement member 131A and the second specimen engagement member 131B to each other. Any suitable alignment pins or other alignment features (such as grooves, protrusions, etc.) may be included on one or more of the first specimen engagement member 131A and the second specimen engagement member 131B to align the first specimen engagement member 131A and the second specimen engagement member 131E with each other and/or the fixture frame 130F. In one aspect, the coupling member 200 may be a shoulder screw or bolt where the shoulder of the screw or bolt functions as a dowel pin and aligns the first specimen engagement member 131A and the second specimen engagement member 131E with each other in a predetermined orientation, while in other aspects, the bushing members 205 are configured to align the first specimen engagement member 131A and the second specimen engagement member 131B with each other.

In one aspect, the least one coupling member 200 is engaged to both the first specimen engagement member 131A and the second specimen engagement member 131B such that a gap G is defined between the first specimen engagement member 131A and the second specimen engagement member 131B, where the first channel 310A and the second channel 310B support the test specimen 150 within the gap G such that at least one opposing major surface 150MJ of the test specimen 150 is visible within the gap G. In one aspect, the first channel 310A and the second 310B channel support the test specimen 150 within the gap G such that both opposing major surfaces 150MJ of the test specimen 150 are visible within the gap G.

In one aspect, a bushing member 205 is disposed between the first specimen engagement member 131A and the second specimen engagement member 131B in any suitable manner to define a size of the gap G. For example, the bushing member 205 may define a width GW of the gap G. In one aspect, the bushing member 205 is selected from any suitable number of different bushing members 205A-205n, each of the number of different bushing members 205A-205n having a size corresponding to a predetermined width W of the test specimen 150 to be tested in the compression test fixture 130. In one aspect, a size (e.g. width GW) of the gap G is adjustable depending on the size of the busing member 205, 205A-205n selected from the number of different bushing members 205A-205n. In one aspect, the bushing member 205 is one or more a cylindrical members configured such that one of the coupling members 200 extends through the bushing member 205 so that the bushing member 205 is held captive between the first specimen engagement member 131A and the second specimen engagement member 131B by a respective coupling member 200.

Referring now to FIGS. 1C, 1D and 6-9, the first channel 310A of the first specimen engagement member 131A includes an alignment surface 600 formed by the side surface 310SB (see FIGS. 3-5) of the first channel 310A. The alignment surface 600 engages and locates the test specimen 150 in the compression test fixture 130, 130' such that a minor surface 150MN of the test specimen 150 that spans the length L of the test specimen 150 is abutted against the alignment surface 600. In one aspect, at least one of the first specimen engagement member 131A and the second specimen engagement member 131B includes an aperture 605 (see also FIGS. 3 and 4), such as a threaded aperture, disposed within the respective first channel 310A and second channel 310B. In one aspect, any suitable alignment member 610, such as a bolt or screw, may be inserted through the aperture 605 of the second specimen engagement member 131B to bias the test specimen 150 in direction 699 against the alignment surface 600 of the first channel 310A of first specimen engagement member 131A. In other aspects, the alignment member 610 may be any suitable biasing member such as a leaf spring or ball detest. As can be seen in FIG. 6 (and FIG. 2A) the first channel 310A and second channel 310B have different depths CD. For example, the first channel 310A has any suitable depth CD1 to support the test specimen 150 from buckling during compression testing while the first channel forms the alignment surface 600 as described above. The second channel 310B is configured with any suitable depth CD2 such that the test specimen 150 has room to expand in direction 698 along the depth CD2 of the second channel during compression testing of the test specimen 150.

Referring to FIGS. 2B and 2C, in one aspect, the first specimen engagement member 131A' and the second specimen engagement member 131B' (which are be substantially similar to first specimen engagement member 131A and the second specimen engagement member 131B) are formed of a first engagement portion 131AP1, 131BP1 and a second engagement portion 131AP2, 131BP2. Each of the first engagement portions 131AP1, 131BP1 is coupled to a respective one of the second engagement portions 131AP2, 131BP2 by one or more screw drives 131D. In one aspect, the screw drive 131D may be non-threadably engaged (i.e. rotatably mounted) to one of the first engagement portion 131AP1, 131BP1 and a second engagement portion 131AP2, 131BP2 while being threadably engaged to the other one of the first engagement portion 131AP1, 131BP1 and a second engagement portion 131AP2, 131BP2 such that as the screw drive 131D is rotated the first engagement portion 131AP1, 131BP1 and a second engagement portion 131AP2, 131BP2 move in direction towards and away from each other to adjust the width CW1, CW2 of a respective first channel 310A and second channel 310B. In other aspects, any suitable drive may be employed in any suitable manner to move the first engagement portion 131AP1, 131BP1 and second engagement portion 131AP2, 131BP2 towards and away from each other in direction 189. In one aspect, the first engagement portions 131AP1, 131BP1 may be coupled to any suitable base plate PLT so that a position of the first engagement portions 131AP1, 131BP1 is fixed relative to the base plate PLT while the second engagement portions 1313AP2, 131BP2 are movably coupled to the base plate PLT for moving towards and away from the respective first engagement portions 131AP1, 131BP1; while in other aspects, the second engagement portions 131AP2, 131BP2 may be coupled to the base plate PLT so that a position of the second engagement portions 131AP2, 131BP2 is fixed relative to the base plate PLT while the first engagement portions 1313AP1, 131BP1 are movably coupled to the base plate PLT for moving towards and away from the respective second engagement portions 131AP2, 131BP2. In one aspect, the base plate PLT may be in the form of fixture frame 130F. As can be seen in FIG. 2C, in this aspect, the first specimen engagement member 131A' and the second specimen engagement member 131B' provide a substantially unobstructed view of the major surfaces 150MJ of the test specimen 150 between and including the ends 150E1, 150E2 of the test specimen 150. In one aspect, each of the first specimen engagement member 131A' and the second specimen engagement member 131B' include any suitable number of guide rods or pins GP that may be used to maintain alignment (e.g. a substantially constant width CW1, CW2 of the first channel 310A and the second channel 310B) of the first engagement portion 131AP1 and the second engagement portion 131AP2 of the first specimen engagement member 131A' and to maintain alignment of the first engagement portion 131BP1 and the second engagement portion 131BP2 of the second specimen engagement member 131B'.

Referring to FIGS. 11A-11C, in one aspect, the first specimen engagement member 131A" and the second specimen engagement member 131B" (which are be substantially similar to first specimen engagement member 131A and the second specimen engagement member 131B) are coupled to a base plate PLT2 or to the fixture frame 130F such that a position of one of the first specimen engagement member 131A" and the second specimen engagement member 131B" does not move or is fixed relative to the base plate PLT or fixture frame 130F while the other one of the first specimen engagement member 131A" and the second specimen engagement member 131B" moves in directions 698, 699 to adjust the width GW between the first specimen engagement member 131A" and the second specimen engagement member 131B". For example, referring to the first specimen engagement member 131A" as an example (noting the second specimen engagement member 131B" is substantially similar), rather than having apertures for two coupling members 200 as described above, the first specimen engagement member 131A" includes a single aperture 1101 to which the screw drive 131D is threadably engaged. The aperture 1101 and the screw drive 131D is located beneath a support plate 1100 on which the test specimen 150 is located during testing, where the support plate 1100 is coupled to the base plate PLT2 or fixture frame 130F. It is noted that the support plate 1100 is selectable from a number of different support plates 1100A, 1100B each having a different width GW1, GW2 corresponding to different widths of test specimens 150. In one aspect, the support plate may extend into the first channel 310A and the second channel 310B to support the test specimen 150. In a manner similar to that above, with respect to FIGS. 2B and 2C, the screw drive 131D may be non-threadably engaged (i.e. rotatable mounted) to one of the first specimen engagement member 131A" and the second specimen engagement member 131B" while being threadably engaged to the other one of the first specimen engagement member 131A" and the second specimen engagement member 131B" such that as the screw drive 131D is rotated the first specimen engagement member 131A" and the second specimen engagement member 131B" move in directions 698, 699 towards and away from each other to adjust the width GW. In other aspects, any suitable drive may be employed in any suitable manner to move the first engagement portion 131AP1, 131BP1 and second engagement portion 131AP2, 131BP2 towards and away from each other in direction 189. In one aspect, each of the first specimen engagement member 131A" and the second specimen engagement member 131B" include any suitable number of guide rods or pins GP that may be used to maintain alignment (e.g. a substantially constant width GW between the first specimen engagement member 131A" and the second specimen engagement member 131B". In this aspect, a substantially unobstructed view of the major surfaces 150MJ of the test specimen 150 between and including the ends 150E1, 150E2 of the test specimen 150 is provided.

In one aspect, an operation of the compression test fixture 130, 130' includes defining the gap G between the first specimen engagement member 131A and the second specimen engagement member 131B of the compression test fixture 130, 130' (FIG. 9, Block 900) with the at least one coupling member 200 engaged to both the first specimen engagement member 131A and the second specimen engagement member 131B. In one aspect, the size of the gap G is determined by a size (e.g. length L and width W) of the test specimen 150 as well as the stiffness of the test specimen 150 such that the expansion of the test specimen 150 in direction 698 during testing is known or can be estimated. One or more bushing members 205 are selected from the number of bushing members 205A-205n where the bushing members define the gap G when the first specimen engagement member 131A and the second specimen engagement member 131B are coupled together by the at least one coupling member 200. The compression test fixture 130, 130' is located on the press 110 in any suitable manner.

The test specimen 150 is inserted into the first channel 310A and the second channel 310B (FIG. 9, Block 910) such that the first channel 310A and the second channel 310B support the test specimen 150 within the gap G such that opposing major surfaces 150MJ of the test specimen are visible within the gap G. The alignment member 610 is moved such that the test specimen moved in direction 699 to engage the test specimen 150 so that the test specimen is located on the alignment surface 600 of the first specimen engagement member 131A. The compression load is applied to the test specimen (FIG. 9, Block 920) in any suitable manner. For example, referring also to FIGS. 1A and 2, the platen 110P of the press 110 is positioned to contact the end 150E1 of the test specimen 150. The alignment member 610 is substantially removed from the second channel 310B such that the test specimen 150 can expand within the second channel 310B (where the alignment member is resilient the alignment member may not have to be removed from the second channel 310B). As the compression load 800 is applied the test specimen 150 is compressed in direction 899 where a change in length ΔL of the test specimen 150 occurs. As the compression load 800 is applied, the test specimen 150 also expands in the direction 698 within the second channel 310B (noting the alignment surface 600 of the first specimen engagement member 131A prevents expansion of the test specimen 150 in direction 699) where a change in width ΔW of the test specimen 150 occurs. Further, as the major surfaces 150MJ of the test specimen 150 are substantially unrestrained, there may be an expansion of the test specimen 150 in direction 898 (see FIG. 1B) as well (such that a change in thickness T occurs), where the compression test fixture 130, 130' provides for stress build up in the test specimen to occur naturally in planes 1, 2, 3 of the test specimen 150. As the test specimen 150 is compressed, strain data in at least one of the opposing major surfaces of the test specimen 150, visible within the gap G, is collected (FIG. 9, Block 930) for viewing and analysis during the compression test.

Referring to FIGS. 10A and 10B an exemplary test specimen 150 is illustrated after a compression test showing a failure 1000 of the test specimen 150 away from the ends 150E1, 150E2 of the test specimen 150. As can also be seen in FIGS. 10A and 10B, because the compression test fixture 130, 130' in accordance with the aspects of the present disclosure provides for stress build up in the test specimen to occur naturally in all planes 1, 2, 3 of the test specimen 150 the failure 1000 exists in all of the planes 1, 2, 3 such that the failure 1000 is a clean fracture substantially free of crumbling of the test specimen 150.

The following are provided in accordance with the aspects of the present disclosure:

A1. A compression test fixture comprising:

a first specimen engagement member having a first channel, the first channel having a first depth;

a second specimen engagement member having a second channel having a second depth that is different than the first depth; and at least one coupling member engaged to both the first specimen engagement member and the second specimen engagement member such that a gap is defined between the first specimen engagement member and the second specimen engagement member, where the first channel and the second channel support the test specimen within the gap such that at least one opposing major surface of the test specimen is visible within the gap.

A2. The compression test fixture of paragraph A1, wherein the first channel includes an alignment surface that engages and locates the test specimen in the compression test fixture.

A3. The compression test fixture of paragraph A2, further comprising an alignment member disposed on the second specimen engagement member, the alignment member being configured to bias the test specimen against the alignment surface of the first channel.

A4. The compression test fixture of paragraph A1, wherein the second depth of the second channel is configured such that the test specimen expands within the second channel during compression of the test specimen.

A5. The compression test fixture of paragraph A1, wherein the first channel has sides defining a width of the first channel that corresponds to a thickness of the test specimen with a predetermined clearance between the sides and the test specimen, the width being configured to prevent buckling of the test specimen.

A6. The compression test fixture of paragraph A1, Wherein the second channel has sides defining a width of the second channel that corresponds to a thickness of the test specimen with a predetermined clearance between the sides and the test specimen, the width being configured to prevent buckling of the test specimen.

A7. The compression test fixture of paragraph A1, wherein the first specimen engagement member has a first end surface, a second end surface and a side surface extending between the first end surface and the second end surface, the first channel being defined in each of the first end surface, the second end surface and the side surface of the first specimen engagement member.

A8. The compression test fixture of paragraph A7, wherein the side surface of the first specimen engagement member includes a recess that intersects the first channel and separates a first portion of the first channel adjacent the first end surface from a second portion of the first channel adjacent the second end surface such that an edge of the test specimen is visible within the recess.

A9. The compression test fixture of paragraph A1, wherein the second specimen engagement member has a first end surface, a second end surface and a side surface extending between the first end surface and the second end surface, the second channel being defined in each of the first end surface, the second end surface and the side surface of the second specimen engagement member.

A10. The compression test fixture of paragraph A9, wherein the side surface of the second specimen engagement member includes a recess that intersects the second channel and separates a first portion of the second channel adjacent the first end surface from a second portion of the second channel adjacent the second end surface such that an edge of the test specimen is visible within the recess.

A11. The compression test fixture of paragraph A1, wherein the at least one coupling member includes a fastener extending through one of the first specimen engagement member and the second specimen engagement member and into the other one of the first specimen engagement member and the second specimen engagement member.

A12. The compression test fixture of paragraph A11, further comprising a bushing member disposed between the first specimen engagement member and the second specimen engagement member, the bushing member defining a size of the gap.

A13. The compression test fixture of paragraph A12, wherein the bushing member is selected from a number of different bushing members, each of the number of different bushing members having a size corresponding to a predetermined width of the test specimen.

A14. The compression test fixture of paragraph A13, wherein a size of the gap is adjustable depending on the size of the busing member selected from the number of different bushing members.

A15. The compression test fixture of paragraph A12, wherein the fastener extends through the bushing member.

A16. The compression test fixture of paragraph A1, further comprising a fixture frame wherein at least one of the first specimen engagement member and the second specimen engagement member are coupled to the fixture frame.

A17. The compression test fixture of paragraph A16, wherein the at least one fastener couples the first specimen engagement member and the second specimen engagement member to the fixture flame such that the first channel and the second channel face each other in an opposing relationship.

A18. The compression test fixture of paragraph A1, wherein the first channel and the second Channel support the test specimen within the gap such that both opposing major surfaces of the test specimen are visible within the gap.

A19. The compression test fixture of paragraph A1, wherein first specimen engagement member includes at least one first support member movably disposed within the first channel, where a position of the at least one first support member within the first channel defines a width of the first channel.

A20. The compression test fixture of paragraph A19, wherein the at least one first support member includes an alignment surface that engages and locates the test specimen in the compression test fixture.

A21. The compression test fixture of paragraph A19, wherein the second specimen engagement member includes at least one second support member movably disposed within the second channel, where a position of the at least one second support member within the second channel defines a width of the second channel.

A22. The compression test fixture of paragraph A21, wherein the at least one second support member includes an alignment surface that engages and locates the test specimen in the compression test fixture.

A23. The compression e t fixture of paragraph A21, wherein:

the at least one first support member comprises a first support member disposed at a first end of the first channel and another first support member disposed at a second end of the first channel; and the at least one second support member comprises a second support member disposed at a first end of the second Channel and another second support member disposed at a second end of the second channel.

A24. The compression test fixture of paragraph A23, wherein:

the first support member disposed at the first end of the first channel is coupled to the second support member disposed at the first end of the second channel so as to be movable as a one piece member; and the other first support member disposed at the second end of the first channel is coupled to the other second support member disposed at the second end of the second channel so as to be movable as a one piece member.

A25. The compression test fixture of paragraph A21, wherein the at least one first support member is coupled to the at least one second support member so as to be movable as a one piece member.

B1. A compression test system comprising:
a frame: and
a test fixture coupled to the frame, the test fixture includes a first specimen engagement member having a first channel, the first channel having a first depth;
a second specimen engagement member having a second channel having a second depth that is different than the first depth; and
at least one coupling member engaged to both the first specimen engagement member and the second specimen engagement member such that a gap is defined between the first specimen engagement member and the second specimen engagement member, where the first channel and the second channel support the test specimen within the gap such that opposing major surfaces of the test specimen are visible within the gap.

B2. The compression test system of paragraph B1, wherein the first channel includes an alignment surface that engages and locates the test specimen in the compression test fixture.

B3, The compression test system of paragraph B2, further comprising an alignment member disposed on the second specimen engagement member, the alignment member being configured to bias the test specimen against the alignment surface of the first channel.

B4. The compression test system of paragraph B1, wherein the second depth of the second channel is configured such that the test specimen expands within the second channel during compression of the test specimen.

B5. The compression test system of paragraph B1, wherein the first channel has sides defining a width of the first channel that corresponds to a thickness of the test specimen with a predetermined clearance between the sides and the test specimen, the width being configured to prevent buckling of the test specimen.

B6. The compression test system of paragraph B1, wherein the second channel has sides defining a width of the second channel that corresponds to a thickness of the test specimen with a predetermined clearance between the sides and the test specimen, the width being configured to prevent buckling of the test specimen.

B7. The compression test system of paragraph B1, wherein the first specimen engagement member has a first end surface, a second end surface and a side surface extending between the first end surface and the second end surface the first channel being defined in each of the first end surface, the second end surface and the side surface of the first specimen engagement member.

B8. The compression test system of paragraph B7, wherein the side surface of the first specimen engagement member includes a recess that intersects the first channel and separates a first portion of the first channel adjacent the first end surface from a second portion of the first channel adjacent the second end surface such that an edge of the test specimen is visible within the recess.

B9. The compression test system of paragraph B1, wherein the second specimen engagement member has a first end surface, a second end surface and a side surface extending between the first end surface and the second end surface, the second channel being defined in each of the first end surface, the second end surface and the side surface of the second specimen engagement member.

B10. The compression test system of paragraph B9, wherein the side surface of the second specimen engagement member includes a recess that intersects the second channel and separates a first portion of the second channel adjacent the first end surface from a second portion of the second channel adjacent the second end surface such that an edge of the test specimen is visible within the recess.

B11. The compression test system of paragraph B1, wherein the at least one coupling member includes a fastener extending through one of the first specimen engagement member and the second specimen engagement member and into the other one of the first specimen engagement member and the second specimen engagement member.

B12. The compression test system of paragraph B11, further comprising a bushing member disposed between the first specimen engagement member and the second specimen engagement member, the bushing member defining a size of the gap.

B13. The compression test system of paragraph B12, wherein the bushing member is selected from a number of different bushing members, each of the number of different bushing members having a size corresponding to a predetermined width of the test specimen.

B14. The compression test system of paragraph B13, wherein a size of the gap is adjustable depending on the size of the busing member selected from the number of different bushing members.

B15. The compression test system of paragraph B12, wherein the fastener extends through the bushing member.

B16. The compression test system of paragraph B1, further comprising a fixture frame wherein at least one of the first specimen engagement member and the second specimen engagement member are coupled to the fixture frame, wherein the at least one of the first specimen engagement member and the second specimen engagement member are coupled to the frame by the fixture frame.

B17. The compression test system of paragraph B16, wherein the at least one fastener couples the first specimen engagement member and the second specimen engagement member to the fixture frame such that the first channel and the second channel face each other in an opposing relationship.

B18. The compression test system of paragraph B1, wherein the first channel and the second channel support the test specimen within the gap such that both opposing major surfaces of the test specimen are visible within the gap.

B19. The compression test system of paragraph B1, further comprising a data collection system disposed adjacent the test fixture, the data collection system including at least one sensing device configured to sense at least one of the opposing major surfaces of the test specimen within the gap.

B20. The compression test system of paragraph B19, wherein the at least one sensing device comprises digital imaging devices.

B21. The compression test system of paragraph B1, wherein the frame comprises a press configured to compress the test specimen held within the test fixture.

B22. The compression test system of paragraph B21, wherein the press includes a platen configured to engage and compress the test specimen.

B23. The compression test system of paragraph B1, wherein first specimen engagement member includes at least one first support member movably disposed within the first channel, where a position of the at least one first support member within the first channel defines a width of the first channel.

B24. The compression test system of paragraph B23, wherein the at least one first support member includes an alignment surface that engages and locates the test specimen in the compression test fixture.

B25. The compression test system of paragraph B23, wherein the second specimen engagement member includes at least one second support member movably disposed within the second channel, where a position of the at least one second support member within the second channel defines a width of the second channel.

B26. The compression test system of paragraph B25, wherein the at least one second support member includes an alignment surface that engages and locates the test specimen in the compression test fixture.

B27. The compression e system of paragraph B25, wherein:

the at least one first support member comprises a first support member disposed at a first end of the first channel and another first support member disposed at a second end of the first channel; and the at least one second support member comprises a second support member disposed at a first end of the second channel and another second support member disposed at a second end of the second channel.

B28. The compression test system of paragraph B27, wherein:

the first support member disposed at the first end of the first channel is coupled to the second support member disposed at the first end of the second channel so as to be movable as a one piece member; and the other first support member disposed at the second end of the first channel is coupled to the other second support member disposed at the second end of the second channel so as to be movable as a one piece member.

B29. The compression test system of paragraph B25, wherein the at least one first support member is coupled to the at least one second support member so as to be movable as a one piece member.

C1. A method for performing a compression test on a test specimen, the method comprising:

defining a gap between a first specimen engagement member and a second specimen engagement member of a compression test fixture with at least one coupling member engaged to both the first specimen engagement member and the second specimen engagement member, where the first specimen engagement member has a first channel having a first depth, and the second specimen engagement member has a second channel having a second depth that is different than the first depth;

inserting a test specimen into the first channel and the second channel such that the first channel and the second channel support the test specimen within the gap such that opposing major surfaces of the test specimen are visible within the gap; and applying a compression load to the test specimen.

C2. The method of paragraph C1, further comprising collecting strain data in at least one of the opposing major surfaces of the test specimen visible within the gap.

C3. The method of paragraph. C1, further comprising aligning and locating the test specimen within at least the first channel with an alignment member disposed on the second specimen engagement member.

C4. The method of paragraph C1, further comprising coupling the first specimen member and the second specimen member to a fixture frame.

C5. The method of paragraph C4, wherein the first specimen engagement member and the second specimen engagement member are coupled to the fixture frame such that the first channel and the second channel face each other in an opposing relationship.

C6. The method of paragraph C1, wherein defining the gap comprises selecting a bushing member from a number of different bushing members, each of the number of different bushing members having a size corresponding to a predetermined width of the test specimen, wherein the bushing member selected defines a size of the gap.

In the figures, referred to above, solid lines, if any, connecting various elements and/or members may represent mechanical, electrical, fluid, optical, electromagnetic, wireless and other couplings and/or combinations thereof. As used herein, "coupled" means associated directly as well as indirectly. For example, a member A may be directly associated with a member B, or may be indirectly associated therewith, e.g., via another member C. It will be understood that not all relationships among the various disclosed elements are necessarily represented. Accordingly, couplings other than those depicted in the drawings may also exist. Dashed lines, if any, connecting blocks designating the various elements and/or members represent couplings similar in function and purpose to those represented by solid lines; however, couplings represented by the dashed lines may either be selectively provided or may relate to alternative examples of the present disclosure. Likewise, elements and/or members, if any, represented with dashed lines, indicate alternative examples of the present disclosure. One or more elements shown in solid and/or dashed lines may be omitted from a particular example without departing from the scope of the present disclosure. Environmental elements, if any, are represented with dotted lines. Virtual (imaginary) elements may also be shown for clarity. Those skilled in the art will appreciate that some of the features illustrated in the figures, may be combined in various ways without the need to include other features described in the figures, other drawing figures, and/or the accompanying disclosure, even though such combination or combinations are not explicitly illustrated herein. Similarly, additional features not limited to the examples presented, may be combined with some or all of the features shown and described herein.

In FIG. 9, referred to above, the blocks may represent operations and/or portions thereof and lines connecting the various blocks do not imply any particular order or dependency of the operations or portions thereof. Blocks represented by dashed lines indicate alternative operations and/or portions thereof. Dashed lines, if any, connecting the various blocks represent alternative dependencies of the operations or portions thereof. It will be understood that not all dependencies among the various disclosed operations are necessarily represented. FIG. 9 and the accompanying disclosure describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, those skilled in the art will appreciate that not all operations described need be performed.

In the foregoing description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or a "third" or higher-numbered item.

Reference herein to "one example" means that one or more feature, structure, or characteristic described in connection with the example is included in at least one implementation. The phrase "one example" in various places in the specification may or may not be referring to the same example.

As used herein, a system, apparatus, structure, article, element, member, or hardware "configured to" perform a specified function is indeed capable of performing the specified function without any alteration, rather than merely having potential to perform the specified function after further modification. In other words, the system, apparatus, structure, article, element, member, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, member, or hardware which enable the system, apparatus, structure, article, element, member, or hardware to perform the specified function without further modification. For purposes of this disclosure, a system, apparatus, structure, article, element, member, or hardware described as being "configured to" perform a particular function may additionally or alternatively be described as being "adapted to" and/or as being "operative to" perform that function.

Different examples of the apparatus(es) and method(s) disclosed herein include a variety of members, features, and functionalities. It should be understood that the various examples of the apparatus(es) and method(s) disclosed herein may include any of the members, features, and functionalities of any of the other examples of the apparatus(es) and method(s) disclosed herein in any combination, and all of such possibilities are intended to be within the scope of the present disclosure.

Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims, if any, are presented for illustrative purposes only and are not intended to limit the scope of the claimed subject matter to the specific examples provided in the present disclosure.

What is claimed is:

1. A compression test fixture comprising:
a first specimen engagement member having a first channel, the first channel having a first depth;

a second specimen engagement member having a second channel having a second depth that is different than the first depth such that a width between sidewalls of the first channel and a width between sidewalls of the second channel, which sidewalls define the respective first depth and second depth, is greater than an end width of a test specimen held within and spanning between the first channel and the second channel; and at least one coupling member engaged to both the first specimen engagement member and the second specimen engagement member such that a gap is defined between the first specimen engagement member and the second specimen engagement member, where the first channel and the second channel support the test specimen within the gap such that at least one opposing major surface of the test specimen is visible within the gap.

2. The compression test fixture of claim 1, wherein the first channel includes an alignment surface that engages and locates the test specimen in the compression test fixture.

3. The compression test fixture of claim 2, further comprising an alignment member disposed on the second specimen engagement member, the alignment member being configured to bias the test specimen against the alignment surface of the first channel.

4. The compression test fixture of claim 1, wherein the second depth of the second channel is configured such that the test specimen expands within the second channel during compression of the test specimen.

5. The compression test fixture of claim 1, wherein the first specimen engagement member has a first end surface, a second end surface and a side surface extending between the first end surface and the second end surface, the first channel being defined in each of the first end surface, the second end surface and the side surface of the first specimen engagement member.

6. The compression test fixture of claim 5, wherein the side surface of the first specimen engagement member includes a recess that intersects the first channel and separates a first portion of the first channel adjacent the first end surface from a second portion of the first channel adjacent the second end surface such that an edge of the test specimen is visible within the recess.

7. The compression test fixture of claim 1, wherein the second specimen engagement member has a first end surface, a second end surface and a side surface extending between the first end surface and the second end surface, the second channel being defined in each of the first end surface, the second end surface and the side surface of the second specimen engagement member.

8. The compression test fixture of claim 7, wherein the side surface of the second specimen engagement member includes a recess that intersects the second channel and separates a first portion of the second channel adjacent the first end surface from a second portion of the second channel adjacent the second end surface such that an edge of the test specimen is visible within the recess.

9. The compression test fixture of claim 1, wherein the at least one coupling member includes a fastener extending through one of the first specimen engagement member and the second specimen engagement member and into the other one of the first specimen engagement member and the second specimen engagement member.

10. The compression test fixture of claim 9, further comprising a bushing member disposed between the first specimen engagement member and the second specimen engagement member, the bushing member defining a size of the gap.

11. The compression test fixture of claim 1, further comprising a fixture frame wherein at least one of the first specimen engagement member and the second specimen engagement member are coupled to the fixture frame.

12. The compression test fixture of claim 1, wherein the first channel and the second channel support the test specimen within the gap such that both opposing major surfaces of the test specimen are visible within the gap.

13. A compression test system comprising:
a frame; and
a test fixture coupled to the frame, the test fixture includes
    a first specimen engagement member having a first channel, the first channel having a first depth;
    a second specimen engagement member having a second channel having a second depth that is different than the first depth such that a width between sidewalls of the first channel and a width between sidewalls of the second channel, which sidewalls define the respective first depth and second depth, is greater than an end width of a test specimen held within and spanning between the first channel and the second channel; and
    at least one coupling member engaged to both the first specimen engagement member and the second specimen engagement member such that a gap is defined between the first specimen engagement member and the second specimen engagement member, where the first channel and the second channel support the test specimen within the gap such that opposing major surfaces of the test specimen are visible within the gap.

14. The compression test system of claim 13, further comprising a data collection system disposed adjacent the test fixture, the data collection system including at least one sensing device configured to sense at least one of the opposing major surfaces of the test specimen within the gap.

15. The compression test system of claim 14, wherein the at least one sensing device comprises digital imaging devices.

16. The compression test system of claim 13, wherein the frame comprises a press configured to compress the test specimen held within the test fixture.

17. A method for performing a compression test on a test specimen, the method comprising:
defining a gap between a first specimen engagement member and a second specimen engagement member of a compression test fixture with at least one coupling member engaged to both the first specimen engagement member and the second specimen engagement member, where the first specimen engagement member has a first channel having a first depth, and the second specimen engagement member has a second channel having a second depth that is different than the first depth;
inserting a test specimen into the first channel and the second channel such that the first channel and the second channel support the test specimen within the gap such that opposing major surfaces of the test specimen are visible within the gap; and
applying a compression load to the test specimen wherein:
    the first channel abuts a first minor surface of the test specimen to restrict widthwise movement of the first minor surface of the test specimen along a direction of the first depth, and a second minor surface of the test specimen, opposite the first minor surface, is free to expand within the second channel in a widthwise direction of the test specimen along a direction of the second depth.

18. The method of claim 17, further comprising collecting strain data in at least one of the opposing major surfaces of the test specimen visible within the gap.

19. The method of claim 17, wherein the first specimen engagement member and the second specimen engagement member are coupled to a fixture frame such that the first channel and the second channel face each other in an opposing relationship.

20. The method of claim 17, wherein defining the gap comprises selecting a bushing member from a number of different bushing members, each of the number of different bushing members having a size corresponding to a predetermined width of the test specimen, wherein the bushing member selected defines a size of the gap.

* * * * *